(12) United States Patent
Klingenbeck-Regn

(10) Patent No.: US 7,684,605 B2
(45) Date of Patent: Mar. 23, 2010

(54) METHOD OF ADJUSTING IMAGE QUALITY OF AN X-RAY IMAGE

(75) Inventor: Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 515 days.

(21) Appl. No.: 10/952,628

(22) Filed: Sep. 29, 2004

(65) Prior Publication Data

US 2005/0069083 A1 Mar. 31, 2005

(30) Foreign Application Priority Data

Sep. 30, 2003 (DE) ................. 103 45 509

(51) Int. Cl.
*G01N 23/04* (2006.01)
(52) U.S. Cl. .............. 382/132; 382/128; 382/133; 378/62; 715/700
(58) Field of Classification Search ............ 382/128, 382/132, 133; 378/62; 715/700
See application file for complete search history.

(56) References Cited

U.S. PATENT DOCUMENTS 5,917,882 A * 6/1999 Khutoryansky et al. ..... 378/116
6,256,372 B1 * 7/2001 Aufrichtig et al. ............ 378/41
2001/0014139 A1 * 8/2001 Price et al. .................. 378/130
2002/0006185 A1 * 1/2002 Lienard et al. ............... 378/205
2002/0094119 A1 * 7/2002 Sahadevan .................. 382/132
2004/0052329 A1 * 3/2004 Almog ........................ 378/38

FOREIGN PATENT DOCUMENTS

EP 0 486 717 A1 5/1992

OTHER PUBLICATIONS

Giordan et al., "Using Adobe Photoshop 5," 1998, QUE, pp. 536-538.*

* cited by examiner

*Primary Examiner*—Samir A. Ahmed
*Assistant Examiner*—John W Lee

(57) ABSTRACT

An intuitively manageable method for adjusting at least one parameter (X) that determines the image quality of an X-ray image produced by an X-ray device (1) is provided, wherein, on a user interface (18) of the X-ray device (1) a setting zone (25) for the parameter (X) is shown pictorially, and in relation to the setting zone (25) the current setting ($X_{act}$) of the parameter (X) is likewise shown pictorially. At least two sub-zones (32, 33, 34) of the setting zone (25) are differentiated from each other by color, wherein a first sub-zone (32) corresponds to a parameter-setting that guarantees good image quality and a second sub-zone (34) corresponds to a parameter-setting that is critical for the image quality.

5 Claims, 2 Drawing Sheets

METHOD OF ADJUSTING IMAGE QUALITY OF AN X-RAY IMAGE

CROSS REFERENCE TO RELATED APPLICATIONS

This application claims priority to the German application No. 10345509.4, filed Sep. 30, 2003 and which is incorporated by reference herein in its entirety.

FIELD OF INVENTION

The invention relates to a method for adjusting at least one parameter of an X-ray device, said parameter determining the image quality of an X-ray image. The invention further relates to a corresponding X-ray device.

BACKGROUND OF INVENTION

The image quality of an X-ray image produced by an X-ray device depends primarily on the dose of radiation that is incident on the X-ray detector when the X-ray is taken. The image quality is particularly good if the dose of radiation falls within a desired range predetermined by the design of the X-ray detector. The dose of radiation again depends firstly on a number of parameters of the X-ray device that can be set, in particular on the voltage and intensity of the X-ray current, the exposure time, etc. Secondly, the dose of radiation depends on the X-ray attenuation, that is, on the absorption of the X-rays by a subject that is arranged between the X-ray beam emitter and the X-ray detector of the X-ray device. In medical applications, the subject is generally a part of a patient's body that is to be examined. In such a case, the X-ray attenuation depends in particular on the size of the patient.

SUMMARY OF INVENTION

To optimize image quality, in a modern X-ray device, an automatic facility is conventionally provided to adjust the parameters of the X-ray device that determine the dose in such a way that the dose of radiation in the X-ray detector is maintained at a constant level. Depending on the depth to which the patient's tissue is irradiated, different parameter settings are achieved, determined by previously established characteristics of the automatic facility.

In certain borderline cases, however, only a relatively poor image quality is achieved by a conventional automatic regulating facility. When X-raying an obese patient, in particular, the X-ray voltage is increased up to the limit by the automatic facility in order to provide the set desired dose. This generally leads to a significant reduction in the image contrast. There is in particular a very considerable reduction in the iodine contrast of vessels that have been filled with iodine-containing contrast.

When X-raying a very obese patient, it may even happen that the preset dose of radiation can no longer be achieved at all, especially as the load limit for the X-ray device has already been reached. In this case the X-ray image has to be taken at a dose of radiation that is lower than the predetermined dose, as a result of which there is a visible increase in the noise level in the X-ray image.

In such a case, however, a certain improvement in the image can often be achieved by manual adjustment of the parameters that determine the dose. In order to allow for such an adjustment, the parameters are usually displayed in alphanumeric form on a user interface, in particular in an object-free zone of a screen image. An X-ray device, in which parameter-setting is provided by means of a user interface that is controllable by an optical cursor or an alphanumeric keyboard, is known, for example, from EP 0 486 717 A1.

Generally, however, such an adjustment can only be achieved successfully in a short enough time if the operator is sufficiently familiar with the X-ray device, especially as the parameters are frequently interdependent in a complex way or there is only limited scope for them to be set independently. In addition to this, the alphanumeric display of the parameters is relatively difficult to follow and it can only be interpreted with a view to improving image quality if the operator is quite familiar with the X-ray device. In practice this represents a considerable disadvantage.

The invention addresses the problem of providing a method for the image-optimizing setting of at least one parameter of an X-ray device, said setting can be achieved simply and intuitively by a user of the X-ray device. The invention further addresses the problem of providing an X-ray device that is suitable for this purpose.

This object according to the invention is achieved by the claims.

According to the above features, on a user interface, which is provided as a component of a control system of the X-ray device, the setting zone is displayed for at least one parameter that determines the image quality of an X-ray image. Furthermore, the current setting of the parameter is shown in relation to said setting range. In order to give the user an intuitively comprehensible impression of the influence of a parameter setting on the image quality, the display of the setting zone of the parameters is divided up into at least two sub-zones that are differentiated from each other by different colors.

A first sub-zone, colored green for example, encompasses here all the parameter settings at which a good image quality is guaranteed. At least one second sub-zone, colored red for example, encompasses those parameter settings that are critical in terms of the image quality of the X-ray image, that is, where a significant deterioration in image quality must be expected.

The setting zone is preferably shown in the form of a bar.

The mode according to the invention, of displaying the parameter or parameters on the user interface, makes it possible for a user of the X-ray device to detect, even without any substantial knowledge of the X-ray device, whether critical conditions relating to image quality are present. If (as is preferred) the setting zone and likewise the current setting of a plurality of parameters are shown at the same time, the user also additionally receives an intuitive impression as to which parameter is critical for the image quality, and as to which dependent relationships exist between the parameters. The user can then alter individual parameters or sets of parameters relatively simply, for example by clicking on the mouse, until the conditions for taking the X-ray are acceptable. The conditions are acceptable in particular when the current settings of all the parameters shown are "in the green zone" of the setting zone or in the vicinity thereof.

To further refine the intuitive method of display, existing interdependent relationships between the parameters that are displayed are preferably likewise shown. Thus, a useful variant of the invention makes provision for a limit, pertaining to the setting zone or to a sub-zone, of at least one parameter to be varied as a function of the current setting of at least one further parameter. Alternatively or additionally, provision is made for a change in the current setting of at least one parameter to lead to at least one further parameter being changed.

The parameters selected for display are one or a plurality of the following parameters in any combination: X-ray dose, tube voltage, tube current (i.e. intensity of the tube current), electrical output of the tube current, distance between the source of the beam and the subject, subsequently referred to as SID (source image distance), or the distance between the source of the beam and the detector, subsequently referred to as FDD (focus detector distance).

BRIEF DESCRIPTION OF THE DRAWINGS

An embodiment of the invention is described below in more detail with the aid of a drawing. The drawing shows.

The components and values are always assigned the same reference signs in the figures.

DETAILED DESCRIPTION OF INVENTION

Figure 1:
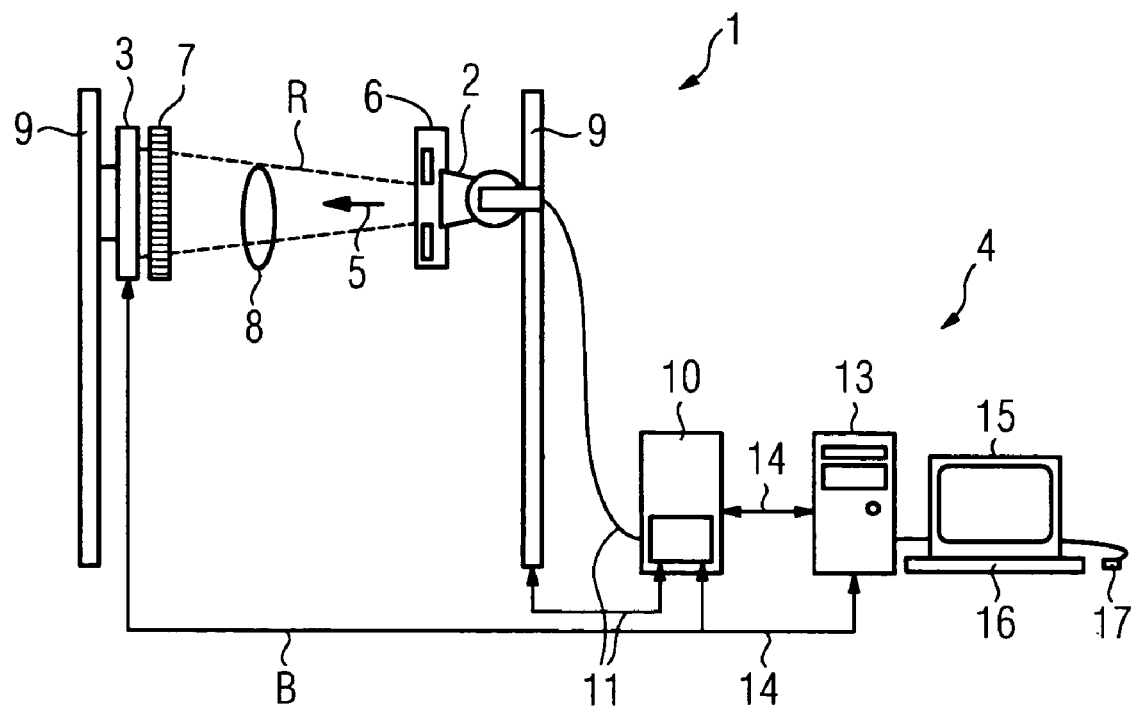
FIG. 1 a diagram of an X-ray device comprising an X-ray detector and a control system, FIG. 2 a user interface of the control system according to FIG. 1 and FIG. 3 by way of illustration, two pictograms (FIGS. 3a and 3b) for intuitive identification of the user interface according to FIG. 2.

The X-ray device 1 shown in diagram form in FIG. 1 comprises an X-ray beam emitter 2, a digital X-ray detector 3 and likewise a control system 4. In the direction of the X-ray beam 5, a collimator 6 and (optionally) a scattered-ray grid 7 are connected in series to the X-ray beam emitter 2 and the X-ray detector 3. In this arrangement, the function of the collimator 6 is to cut out a part of a desired size of the beam of the X-ray radiation R produced by the X-ray beam emitter 2, which passes through a person 8 who is to be examined or an object that is to be examined, and through the scattered-ray grid 7, onto the X-ray detector 3. In this arrangement, the function of the scattered-ray grid 7 is to cut out lateral scatter, which would distort the X-ray image that is incident on the X-ray detector 3.

The X-ray beam emitter 2 and the X-ray detector 3 are adjustably fixed to a support 9 or adjustably fixed above or below an examination table.

The control system 4 comprises a power unit 10 to actuate the X-ray beam emitter 2 and/or the X-ray detector 3 and also to produce a tube current that is supplied to the X-ray beam emitter 2 to create the X-ray radiation R. The power unit 10 is connected by data and power lines 11 to the X-ray beam emitter 2. The control system 4 further comprises a data processing device 13. The data processing device 13 comprises routines for the control and operation of the X-ray device 1 and also routines for the evaluation of the image data B taken by the X-ray detector 3. The data processing device 13 is connected by data and system bus lines 14 to the power unit 10 and the X-ray detector 3. For the input and output of data, it is further connected to peripheral devices, in particular to a screen 15, to a keyboard 16 and to a mouse 17.

The X-ray detector 3 is in particular a digital X-ray detector, as is in fact known from M. Spahn, et al., "Flachbilddetektoren in der Röntgendiagnostik" (Flat screen detectors in X-ray diagnosis), *Radiologe*, 43 (2003), p. 340-350.

Figure 2:
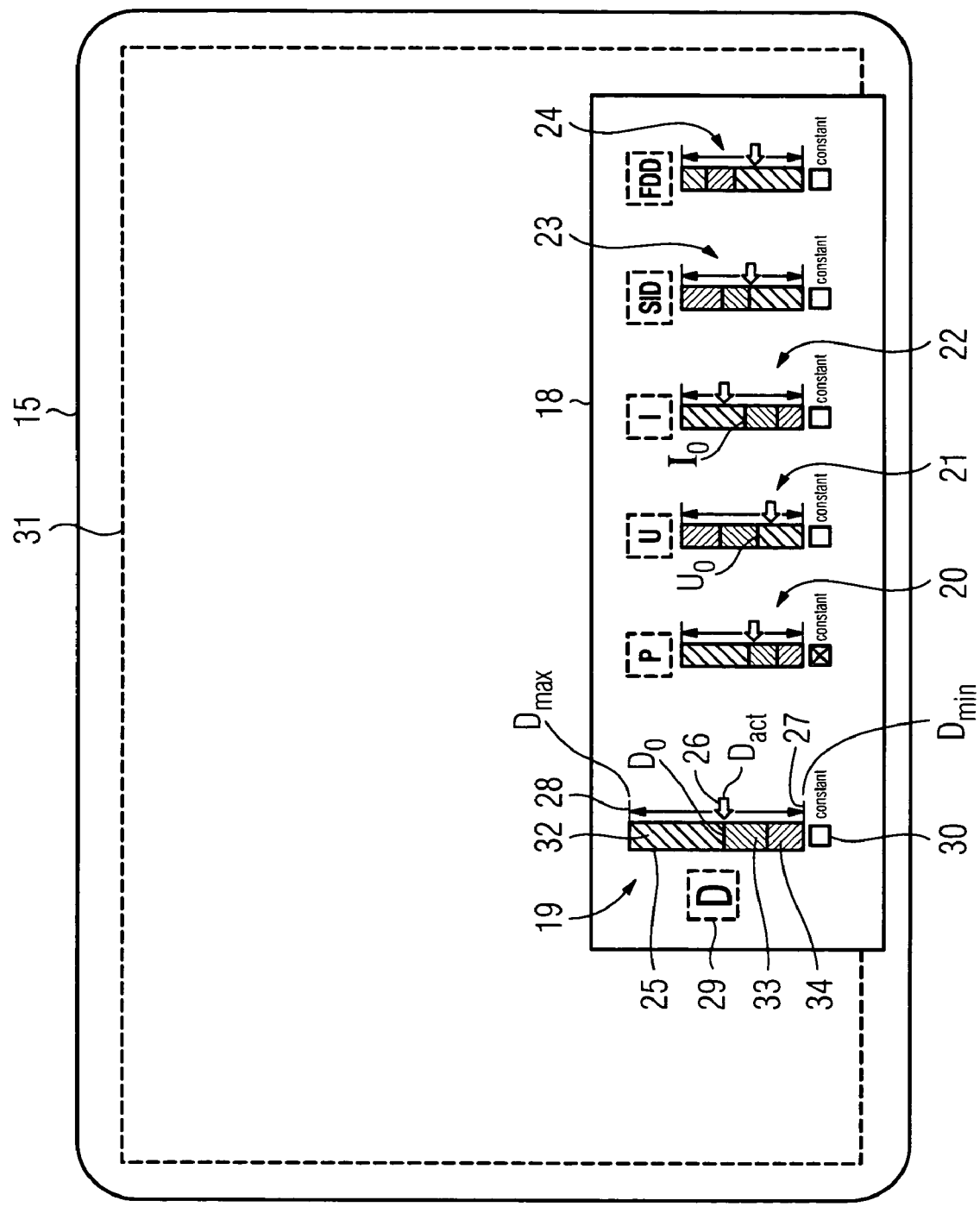

The control system 4 comprises a user interface 18, which is shown in diagram form in FIG. 2. The user interface 18 that is shown in FIG. 2 is a virtual user interface, which is displayed on a section of the screen 15. The user interface 18 comprises a plurality of controls 19 to 24, which are modeled on slide controls. The function of each control 19 to 24 is to set a parameter (X) (X=D, P, U, I, SID, FDD) that influences the image quality of an X-ray image that is to be taken by the X-ray device 1. These parameters X include the dose of radiation D impinging on the X-ray detector 3, the electrical power P from the tube current provided by the power unit 10, the tube voltage U, the intensity of the tube current (referred to below in short as I), the SDI (source image distance) between the X-ray beam emitter 2 and the person 8 or object that is to be examined and the FDD (focus detector distance) between the X-ray beam emitter 2 and the X-ray detector 3.

Each control 19 to 24 comprises a setting zone 25 that is shown as a bar, a cursor 26, which displays the current setting $X_{act}$ ($X_{act}=D_{act}$, $P_{act}$, $U_{act}$, ...) of the respective parameter (X) that is assigned thereto. By operating the mouse 17 or the keyboard 16, the cursor 26 can be moved between a lower stop 27 and an upper stop 28. Depending on the position of the cursor 26 in relation to the setting zone 25, the respective parameter (X) is adjusted between a lower limit $X_{min}$ ($X_{min}=D_{min}$, $P_{min}$, $U_{min}$, ...), corresponding with the lower stop 27, and an upper limit $X_{max}$ ($X_{max}=D_{max}$, $P_{max}$, $U_{max}$, ...), corresponding with the upper stop 28. Each control 19 to 24 further comprises an identification field 29, that has an inscription showing the respective parameter (X) and an activation box 30, through the activation of which (using a mouse 17 or keyboard 16) each respective parameter can be maintained at a constant level.

The user interface 18 can be minimized or maximized in relation to the screen surface in a manner that is in fact known, as desired by a user, and can be arranged anywhere on the screen 15 and, where necessary, can also be blanked out. In this way, the user interface 18 can always be arranged such that it does not cover any essential zones of an image zone 31 that forms the screen background, said zone being provided to display an X-ray image.

In order to allow intuitive use of the X-ray device 1, the setting zone 25 of each control 19 to 24 is divided into three sub-zones 32, 33 and 34 which are differentiated from each other by color. The first sub-zone 32 marks a range of settings of the respective parameter (X), in which an acceptable image quality is guaranteed. The opposite sub-zone 34 marks a range of parameter settings, in which the image quality of the X-ray image is significantly restricted. The intermediate sub-zone 33 marks an intermediate range of parameter settings, in which a slight restriction in image quality has to be expected.

According to the usual convention, the non-critical sub-zone 32 is preferably colored green, whilst the critical sub-zone 34 is red, and the intermediate sub-zone 33 is colored yellow. The allocation of the colors is arbitrary, however.

The parameters (X) cannot generally be adjusted independently of one another. The current setting 26 of a parameter (X) usually depends, rather, on the current settings 26 of the other parameters (X). In particular, the equation for the dose of radiation D is approximately $$D = \frac{c}{a} \cdot U^2 \cdot I = \frac{c}{a} \cdot U \cdot P \qquad \text{Formula 1}$$

Here, c is a dimensional function that is dependent on the distances SID and FDD. The variable a stands for the reduction, in other words the absorption of the X-ray radiation R in the tissue of the person to be examined 8 or in the material that makes up an object that is to be examined. The power P again depends, according to the well-known equation $$P = U \cdot I \qquad \text{Formula 2}$$

on the tube voltage U and the tube current I.

As a result of the fact that the parameters (X) are internally dependent on one another, a change in the current setting $X_{act}$ of one parameter (X) generally leads to a consequential change in other parameter settings. Thus, for instance, an increase in the tube current I and/or the tube voltage U leads to an increase in the power P, and this again to an increase in the dose D.

By activating an activation box 30, the respective parameter (X) can be maintained at a constant level. In this way, an (unwanted) consequential adjustment of said parameter (X) can be avoided.

The limits $X_{min}$ and $X_{max}$ of each parameter (X) are determined by the design of the X-ray device 1.

The way the sub-zones 32, 33 and 34 are distributed over the whole setting zone 25 has to be determined individually for each parameter (X), and for each respective control 19 to 24, by means of empirical tests with the specific X-ray device 1 and/or by model calculations.

The lower limit of the "green" sub-zone 32 of the control 19 is preferably set at a predetermined desired value $D_0$ for the dose of radiation D. The "yellow" sub-zone 33 incorporates a reduction in dose of up to 50% compared with the desired value $D_0$. A reduction in dose of over 50% compared with the desired value $D_0$ is recorded on the "red" sub-zone 34.

For a good image contrast in the X-ray image that is to be taken, the tube voltage U should be maintained as low as possible. The upper limit of the "green" sub-zone 32 of the control 21 is preferably set at a threshold value $U_0$, at which the desired value $D_0$ is reached at maximum power $P_{max}$. The threshold value $U_0$ can be derived simply from Formula 1 and hence:

$$U_0 = \frac{a \cdot D_0}{c \cdot P_{max}} \qquad \text{Formula 3}$$

It should be noted that Formula 3 depends on the patient-dependent reduction a and the distance-dependent function c. In the determination of the threshold value $U_0$, the reduction a is usefully estimated by a constant that corresponds to the reduction in a standard patient. The function c can likewise be estimated using standard values for SID and FDD. Alternatively, the limit $U_0$ can be set so that it can be varied depending on the current settings $SID_{act}$ and $FDD_{act}$.

The lower limit of the "green" sub-zone 32 of the control 22 is preferably set at a threshold value $I_0$ of the tube current I, at which the desired value $D_0$ of the dose of radiation D is achieved at a maximum output $P_{max}$ and minimum tube voltage $U_0$:

$$I_0 = \frac{P_{max}}{U_0} = \frac{c}{a} \cdot \frac{P_{max}^2}{D_0} \qquad \text{Formula 4}$$

In a similar manner the sub-zones 32, 33 and 34 are set for controls 20, 23 and 24.

In standard operation of the X-ray device 1, the parameters (X) are preset by an automatic mechanism that is not shown in closer detail, such that the current setting $X_{act}$ of each parameter (X) falls, where possible, within the respective "green" sub-zone 32. In borderline cases, in particular when examining obese or very obese patients, in whom this target setting cannot be achieved by the automatic mechanism, by moving the cursor 26 of the respective control 19 to 24, the user of the X-ray device 1 can make a manual adjustment to the parameters (X), in order to optimize the image quality of the X-ray image that is to be taken.

Figure 3A:
Figure 3B:
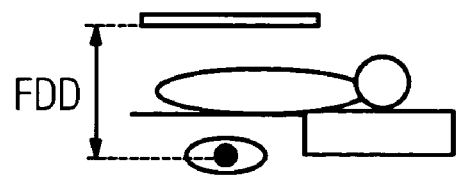

In order to improve the intuitive ease of operation of the user interface 18, instead of the alphanumeric designation for the identification fields 29 that is shown in FIG. 2, designation with pictograms is used at least for individual parameters (X). Such a pictogram that can be used to designate the control 23 and which shows the distance SID pictorially is shown, for example in FIG. 3a. A pictogram which shows in a similar manner the distance FDD, and which can be used to designate the identification field 29 for the control 24 is shown in FIG. 3b.

The invention claimed is:

1. A method of adjusting an image parameter of an X-ray image, comprising:
   displaying a virtual user interface on a screen;
   displaying a setting range of the image parameter, the setting range having at least a first and a second range subset, the subset ranges including different coloring, the first subset representing a recommended parameter setting range and the second subset representing a non recommended parameter setting range; and
   displaying a current parameter setting of the image parameter relative to the parameter setting range, on the user interface;
   wherein the image parameter is related to an element of the group consisting of an X-ray dose, a X-ray tube voltage, an X-ray tube current, an electrical power, a distance between an X-ray emitter and a patient to be examined, a distance between an X-ray emitter and an X-ray detector, an X-ray pre-filtering and an X-ray exposure time
   wherein a plurality of image parameters is displayed in parallel;
   wherein a limit value of the range subsets of the parameter setting ranges of a first of the image parameters is calculated using the current parameter setting of a second of the image parameters;
   wherein one of the range subsets of the parameter setting ranges of said first of the image parameters is calculated using the current parameter setting of said second of the image parameters; and
   wherein the current parameter setting of said first of the image parameters is adjusted by the current setting of said second of the image parameters.

2. The method according to claim 1, wherein the recommended parameter setting range corresponds to a high image quality of the X-ray image.

3. The method according to claim 1, wherein the non recommended parameter setting range corresponds to a low image quality of the X-ray image.

4. The method according to claim 1, wherein the parameter setting range is displayed as a bargraph.

5. An X-ray device for processing an X-ray image, comprising:
   an X-ray emitter;
   an X-ray detector; and
   a virtual user interface for adjusting an image parameter of the X-ray image, the virtual user interface adapted to:
   display a parameter setting range having at least a first and a second range subset, the subset ranges including different coloring, the first subset representing a recommended parameter setting range and the second subset representing a non recommended parameter setting range, and
   display a current parameter setting of the image parameter relative to the parameter setting range, on the user interface
   wherein the image parameter is related to an element of the group consisting of an X-ray dose, a X-ray tube voltage, an X-ray tube current, an electrical power, a distance between an X-ray emitter and a patient to be examined, a distance between an X-ray emitter and an X-ray detector, an X-ray pre-filtering and an X-ray exposure time wherein a plurality of image parameters is displayed in parallel; wherein a limit value of the range subsets of the parameter setting ranges of a first of the image parameters is calculated using the current parameter setting of a second of the image parameters;

wherein one of the range subsets of the parameter setting ranges of said first of the image parameters is calculated using the current parameter setting of said second of the image parameters; and wherein the current parameter setting of said first of the image parameters is adjusted by the current setting of said second of the image parameters.

* * * * *